United States Patent [19]

Litwack et al.

[11] Patent Number: 4,740,306

[45] Date of Patent: Apr. 26, 1988

[54] CHROMATOGRAPHIC COLUMN

[75] Inventors: Gerald Litwack, Bryn Mawr; Ted M. Kirsch, Philadelphia, both of Pa.

[73] Assignee: Temple University - of the Commonwealth System of Higher Education, Philadelphia, Pa.

[21] Appl. No.: 840,399

[22] Filed: Mar. 17, 1986

[51] Int. Cl.$^4$ .............................................. B01D 15/08
[52] U.S. Cl. .................. 210/198.2; 210/290; 210/635; 210/656; 435/219; 435/803; 435/815; 436/501; 530/396; 530/413; 530/417
[58] Field of Search ............... 210/635, 656, 657, 659, 210/198.2, 283, 290; 55/67, 386; 436/501; 435/219, 317, 320, 803, 815; 530/395, 396, 413, 417

[56] References Cited

U.S. PATENT DOCUMENTS

| | | | |
|---|---|---|---|
| 3,787,317 | 1/1974 | Jaworek | 210/31 |
| 3,902,849 | 9/1975 | Barak | 210/198.2 |
| 3,957,741 | 5/1976 | Rembaum et al. | 526/312 |
| 3,959,079 | 5/1976 | Mareschi et al. | 195/63 |
| 4,016,149 | 4/1977 | Travis et al. | 260/122 |
| 4,086,222 | 4/1978 | Lindquist et al. | 260/122 |
| 4,225,487 | 9/1980 | Cuatrecasas et al. | 260/121 |
| 4,276,059 | 6/1981 | Firca et al. | 23/230 |
| 4,301,139 | 11/1981 | Feingers et al. | 424/1 |
| 4,486,311 | 12/1984 | Nakajima et al. | 210/635 |
| 4,510,131 | 4/1985 | Donahoe | 530/417 |

OTHER PUBLICATIONS

Grandic, "Purification of the Unactivated Glucocorticoid Receptor and its Subsequent in Vitro Activation", Journal of Biological Chemistry, vol. 259, No. 5, Mar. 10, 1984, pp. 3173-3180.

Primary Examiner—Ernest G. Therkorn
Attorney, Agent, or Firm—Seidel, Gonda, Goldhammer & Abbott

[57] ABSTRACT

A chromatographic column and process for isolating or purifying steroid hormone or cell membrane receptors using the column are provided in which the column contains at least three resin layers between the inlet and the outlet ends of the column, the layer closest the inlet being a strong cationic exchange resin, the middle layer being a matrix containing a triazine dye that will bind proteases and proteins with dinucleotide fold conformations, and the layer closest the outlet being a weak anionic exchange resin, the ratio of the volumes of the resin layers being 1:2:1.

13 Claims, 1 Drawing Sheet

CHROMATOGRAPHIC COLUMN

The invention was supported in part by grants 1 RO1 AM 32870 and 1 RO1 AM 13531 from the National Institute of Arthritis, Diabetes and Digestive and Kidney Diseases of the National Institutes of Health; by grant PCM-8215844 from the National Science Foundation; and by a Core Grant, CA-12227, to the Fels Research Institute from the National Cancer Institute, National Institutes of Health.

This invention relates to the selective purification of solubilized steroid hormone receptor complexes and solubilized cell membrane receptor complexes (liganded receptors) from crude cytosolic or particulate membrane fractions.

Several procedures are currently available for the purification of activated (DNA-binding) glucocorticoid receptors but all involve chromatography on DNA-cellulose and ion exchange chromatography. These processes involve either one step ion exchange chromatography or DNA-cellulose column chromatography. The conventional method for a high level of purification of unactivated hormone receptors involves the use of a steroid selective affinity resin, followed by gel filtration, and ion exchange chromatography. Affinity chromatography generally requires that a matrix be tailor made to the desired receptor, a process that can consume years of development effort. Furthermore, affinity chromatographic procedures can consume upwards of twenty four hours, during which time the protein of interest is exposed to cytosolic proteases and phosphatases. The use of such methods for the isolation of glucocorticoid hormone receptors from cytosol are expensive, time consuming and tend to produce degradation products as well as the desired result.

Specialized affinity resins that are complex and extremely expensive to produce are known for such applications. However, because they are not readily available and only produced in relatively small laboratory batch-type processes, such materials are not adequate for commercial application at a reasonable cost.

A new procedure utilizing a unique chromatographic construction that will permit rapid, selective, and relatively inexpensive isolation of both activated and unactivated forms of steroid hormone and cell membrane receptors, particularly glucocorticoid receptors has now been found. The new construction is a chromatographic column containing a matrix of at least three resin layers in a specific ratio and disposition with respect to one another. The resin layer closest the inlet of the column is a strong cationic exchange resin, preferably a phosphorylated ($-PO_4H_2^-$) gel, most preferably a six percent phosphorylated agarose gel crosslinked with epichlorohydrin. The middle or next adjacent layer is a monochlorotriazine dye on a support, that will bind proteases and proteins with dinucleotide fold conformations. The layer closest the outlet end of the column is a weak anionic exchange resin, preferably a diethylminoethyl(DEAE)-containing matrix. The most preferred support for the monochlorotriazine dye and the DEAE ion is a copolymer of N-acryloyl-2-amino-2-hydroxymethyl-1,3-propanediol with the dye or any suitable DEAE-containing monomer. The ratio of the volumes of the respective resin layers is 1:2:1, and a preferred construction contains a ratio of 20:40:20.

The construction of the invention is further illustrated by reference to the accompanying drawings in which like numerals refer to like components. The construction of the invention may utilize either commercially available closed-system columns (substantially no space exists between the top of the resin layers and the plunger) as in FIG. 1, or may employ an easily fabricated chromatographic column with a hypodermic syringe (preferably plastic) fitted with a stopper as in FIG. 2.

Figure 1:
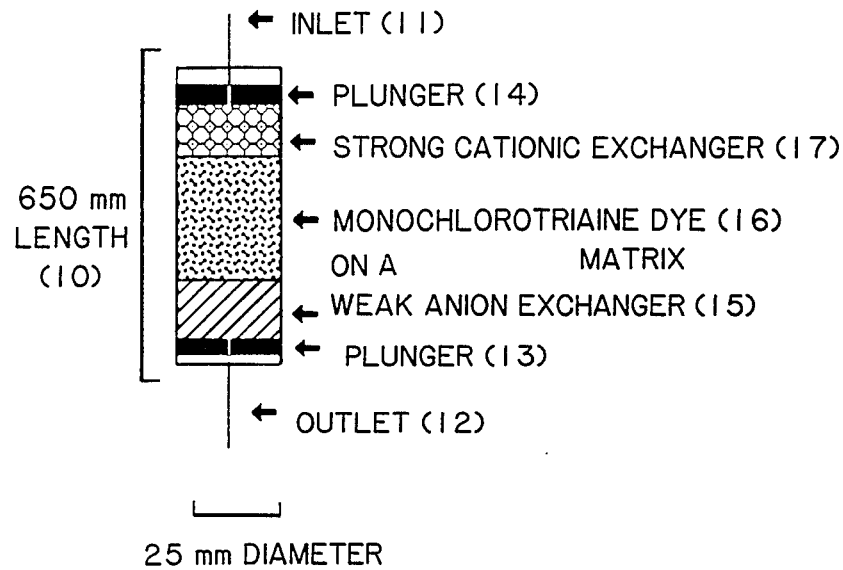
FIG. 1 is a longitudinal cross-section of a commercial closed-system chromatographic column of the invention.

In FIG. 1, column 10 is a 650 mm long glass column having an internal diameter of 25 mm. The column is open at the inlet end 11 and the outlet end 12. The outlet is fitted with a plunger 13 on top of which is a layer 15 of a weak anionic exchange resin. On top of layer 15 is layer 16 of a matrix complexed with monochlorotriazine dye. Layer 17 is a strong cationic exchange resin which is closed by a plunger 14 at the inlet 11.

Figure 2:
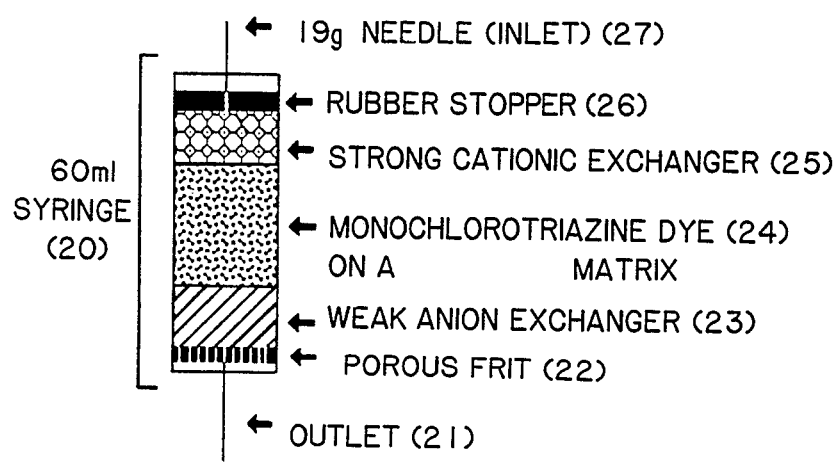
FIG. 2 is a longitudinal cross-section of a fabricated open-system chromatographic column (some space, minimized as much as possible, existing between the top of the resin layers and the stopper).

In FIG. 2, column 20 is a plastic 60 ml hypodermic syringe having an outlet 21 separated from the resins by a porous frit 22. A layer 23 of the weak anionic exchange resin is situated on top of the frit 22. A layer 24 of a matrix complexed with a monochlorotriazine dye is located on top of layer 23. Top layer 25 is a strong cationic exchange resin closed by a rubber stopper 26 containing a 19 gauge syringe needle 27 which serves as an inlet.

As used herein, the term receptors refers to steroid hormone receptors and cell membrane receptors which, in turn, refer to solubilized steroid hormone receptors complexed with appropriate ligands and solubilized cell membrane receptors complexed with appropriate ligands, respectively.

The term cytosol refers to the receptors in their unactivated form.

The term salt gradient refers to a salt in increasing concentration which changes the ionic nature of the bond between the receptor and the matrix, freeing the receptor from the binding site at a characteristic salt concentration. Any elutropic salt may be used including, for example, sodium chloride, sodium thiocyanate, potassium phosphate, sodium acetate, potassium acetate, and any others known in the art.

The process of the invention using the unique chromatographic structure described herein involves flowing the composition or solution to be purified, or from which the steroid hormone receptor or cell membrane receptors are to be isolated, through the chromatographic column of this invention so that the composition or solution is allowed to pass through and contact the three resin layers. The steroid hormone receptors and some cell membrane receptors are bound to separate layers of resin separated from the basic proteins while neutral proteins including neutral cell membrane receptors flow through and exit the column. The neutral receptors which pass through the column are then collected. The bound receptors are eluted from the chromatographic column. For elution, a salt exchange may be carried out either stepwise, using increasing concentrations of an elutropic salt (for example, using potassium phosphate buffer at pH 7 at 50 mM, then 100 mM, then 200 mM), or with a salt gradient.

The process of the invention can be completed within sixty to ninety minutes with 100-400 fold purification. The process of this invention therefore provides a separation/purification procedure that is both rapid and selective, and that can be carried out without specialized technical experience.

Although the component resins of the new column have been used individually in protein purification, they have not been used in a construction such as that described herein to provide an inexpensive, one-step procedure to isolate the unactivated non-DNA binding form of the receptors. Further, the practice of this invention makes possible the isolation of steroid hormone and cell membrane receptors based on removal of non-specific proteins without the need to tailor make the chromatographic matrix to respond specifically either to the crude tissue extract or the receptor to be be separated from it. The yields and extent of purification are equivalent to or better than yields obtained in the time-consuming affinity gel procedure and the invention reduces the time of exposure of the receptors to harmful proteases and other enzymes which could affect the final product. Pre-binding of the cytosol with steroidal ligand stabilizes the receptor upon storage.

The process and construction of this invention provide a quick and easy initial separation of the desired receptors from crude tissue extract, but even higher purification levels can be achieved by simply repeating the extraction process using the unique column construction of this invention. Alternatively, if very high purification levels are desired, the crude extract can be subjected to gel filtration before the separation of this invention and virtual homogeneity can be achieved with gel filtration through, for example Sephadex-75 followed by DEAE-cellulose column chromatography. Further, while it is not possible to purify the liganded receptor easily and quickly using prior art procedures such as an affinity resin process, without producing degradation products, it is possible quickly and easily to purify the liganded receptor with the column of this invention without producing degradation products in the process.

The sequence of the resins with respect to one another and in the prescribed proportions is important if optimum results are to be obtained. In the practice of this invention the resins are disposed in a single column so that one part of (A), a strong cationic exchange resin, preferably containing phospho functional ions, is located at the top or inlet end of the column. Two parts of (B) a triazine dye, preferably containing monochlorotriazine, are located between (A) and one part of (C), a weak anionic exchange resin, preferably containing DEAE functional groups. Any matrices known to those skilled in the art may be used to support the phospho-, triazine dye, or diethylaminoethyl groupings. Synthetic supports are preferred since they have been found to allow maximum flow characteristics. Resins synthesized by the free radical copolymerization of a primary monomer, N-acryloyl-2-amino-2-hydroxymethyl-1,3-propanediol, and the triazine dye or a suitable DEAE-containing monomer, preferably formed into rigid beads with diameters between 40 and 80 μm, are preferred. Some such resins are known as DEAE- and blue-Trisacryl M (Tm) ion exchangers. Other resins such as 6% agarose gels cross-linked with epichlorohydrin and phosphorylated to an acid equivalent of 100-150 μeq/ml gel and having a pH of 2-13 can also be used, preferably in the form of beads having a size of 60-140 μm. Some such resins are known as phospho-Ultragel A6R (Tm) ion exchangers. Other matrices such as sepharose gels, agarose, cross-linked agarose, polyacrylamide agarose copolymers, cross-linked dextran, cross-linked dextran containing polyacrylamide bridges, cellulose, cellulose resins, and cellulosics can also be used.

It is to be understood that other materials that will not interfere with the operation of the column in accordance with this invention may also be used in the columns of this invention as desired. For example, additional resins, porous frits, and any other materials that will not interfere with the operation of the unique structure of this invention may also be employed. However, since the three components in the ratios and relationship outlined above are important, the structure is generically referred to as a tricolumn even though other materials may be present.

The structure of this invention can be fabricated by any of the methods conventionally employed for packing chromatrographic columns into any of the sizes conventionally used given the material to be treated and the components to be isolated or purified. A preferred structure for treating 20 to 50 ml aliquots is a 650 mm long glass column with an inside diameter of 25 mm containing a matrix resin layer ratio of 20:40:20.

Steroid hormone receptors or solubilized cell membrane receptors can be purified or isolated from crude tissue extract using the process of this invention. Steroid hormone receptors for such ligands as aldosterone, glucocorticoid, progesterone, testosterone, estrogen and the like, and cell membrane receptors for such ligands as leukotrienes, glucagon, and insulin from tissue extracts may be isolated by the preactice of this invention. Tissue extractions may be performed as described in *Methods of Enzymology*, v. 36, 1975, O'Malley and Hardman eds., Academic Press, N.Y. The salt concentration of the buffer should be below or equal to that given by a 50 mM potassium phosphate buffer before application to the tricolumn to insure appropriate binding of receptors. For best results, the resins should be washed thoroughly to remove all proteins which do not bind to the various matrices in the tricolumn; this may be monitored spectrophotometrically and should be at least one column volume of buffer. Proteins bound to the ion exchange resin may be eluted in the range of 100 mM to 500 mM potassium phosphate buffer. Steroid hormone receptors elute in the 100 mM to 300 mM range.

The steroid hormone or cell membrane receptors isolated and/or purified by the practice of this invention may be used in studies of ligand-receptor functions which include growth, differentiation, homeostasis and pathological processes involving tumorigenesis and rheumatic disorders.

The invention is further illustrated but is not intended to be limited by the following examples in which all procedures are performed at 0° C. in a cold box or cold room and all parts and percentages are by weight unless otherwise specified.

EXAMPLE 1

Preparation of a Tricolumn

A commercially available closed system column as shown in FIG. 1 is used. The column is a 650 mm long glass chromatographic column having an inside diameter of 25 mm. A slurry of an anion exchange resin of (A)

a free radical polymerization product of N-acryloyl-2-amino-2-hydroxymethyl-1,3-diol containing DEAE ions as the weak anionic exchange resin is poured into the column to form a bed. Supernatant is drained from the bottom of the column by gravity. Thereafter, (B) a free radical polymerization product of N-acryloyl-2-amino-2-hydroxymethyl-1,3-diol containing ions of a monochlorotriazine dye is slowly added to the packed bottom layer by pouring a slurry of the complexed matrix material down the side of the column and draining the supernatant as above until the layer of (B) is twice the height (volume) of the layer below it. A final slurry of (C) a six percent phosphorylated agarose gel crosslinked with epichlorohydrin as the strong cationic exchange resin is poured into the column and drained as above to form a layer one-half the height (volume) of the layer below it. The column is then closed with a plunger top which facilitates packing. In an open system (FIG. 2), the column is closed with a stopper containing a needle extending to the top of the uppermost layer.

The packed resins (tricolumn) are equilibrated by pumping 150 ml of starting buffer (Buffer A) through the tricolumn at a rate of 5 ml/minute. Buffer A contains 50 mM of potassium phosphate, 10 mM of sodium molybdate, 10 mM of thioglycerol, and has a pH of 7. Unactivated glucocorticoid receptor complexes from cytosol are in the 50 mM potassium phosphate buffer. The sodium molybdate is an inhibitor of proteases and phosphatases and prevents activation of steroid hormones to the DNA-binding form.

Preparation of the Cytosol

Male Sprague-Dawley rats (250 g) are adrenalectomized five days prior to sacrifice. Following sacrifice, the livers are perfused with Buffer A, excised, weighed, and homogenized in two volumes of Buffer A (w/v; g/ml). (Five rats yield about 85 g of liver tissue.) The homogenate is centrifuged at 10,000 g for ten minutes to remove nuclei and cellular debris. The supernatant is then centrifuged at 100,000 g for sixty minutes. The straw-colored supernatant containing the glucocorticoid hormone receptor is the cytosol.

Purification of the Glucocorticoid Receptor Complex Affinity Gel Procedure

The cytosol prepared as described above is treated as described by Grandics et al, *J. Biol. Chem.*, Vol. 259, No. 5, pp. 3178–3180, 1984. Briefly, the cytosol is incubated with deoxycorticosterone affinity resin gel in a ratio of 2:1 (v/w; ml/g) overnight. The gel is washed extensively (Buffer A, 8×20 ml washes) and the bound glucocorticoid receptor complex is eluted from the resin gel with 14 ml of Buffer A containing triamcinolone acetonide (TA), a synthetic glucocorticoid. The synthetic glucocorticoid is labelled with a radioisotope using the hormonal steroid ligand to enable identification of the receptor complex through the isolation procedure. Beta radioactive decay rates are measured by scintillation counting. In the case of the glucocorticoid receptor, 100 nM tritium labelled triamcinolone acetonide (2 $\mu$M TA, 44 Ci/mmol TA; NEN division, E. I. du Pont de Nemours and Company), hereinafter [$^3$H]-TA, is used. The affinity resin gel eluate (14 ml) containing glucocorticoid receptor complexed with [$^3$H]-TA is quantitated by hydroxylapatite (HA) binding assay (400 $\mu$l of a 25% slurry of HA in Buffer A at a ratio of 50 $\mu$l eluate/400 ul of HA slurry; pelleted, washed three times, and pellet counted). Total binding (100 nM [$^3$H]-TA) and non-specific binding (+10 $\mu$M radioinert TA) are determined separately. Non-specific binding is routinely 5% of the total binding. The results are presented in TABLE I.

Tricolumn Procedure

The cytosol (8.4 ml) prepared as described above, is labelled with [$^3$H]-TA (100 nM; two hours at 0° C.) to monitor the elution of the glucocorticoid receptor complex. The cytosol is pumped at the rate of 5 ml/minute onto a tricolumn, constructed and equilibrated as described above, and containing 20:40:20 volumes of A:B:C. The column is washed with 7 ml fractions of Buffer A until all unbound cytosolic proteins are collected (most conveniently measured by absorbance at 280 nm as reflected by a return to baseline on a strip chart recorder; the flow cell must have a reference chamber since sodium molybdate absorbs strongly at 280 nm); this requires about 100 ml of Buffer A. About 50% of non-receptor protein flows through the column at this stage but all of the steroid hormone receptor is retained separately on the anion exchange resin.

The column is then washed with 100 ml of Buffer A adjusted to contain a 100 mM concentration of potassium phosphate. About 5% of the total non-receptor proteins are eluted at this step. Finally, the glucocorticoid receptor complex is eluted with 3 ml portions of Buffer A, adjusted to contain a 200 mM concentration of potassium phosphate, until a total of 75 ml of Buffer A is used. The receptor is eluted completely in three to four of the fractions with concentration of the receptor in several fractions. Purity of the receptor is assessed by SDS-PAGE (sodium dodecyl sulfate polyacrylamide gel electrophoresis) followed by staining using a sensitive Coomassie-Silver double stain. The results are presented in TABLE I.

TABLE I

| Purification of the Glucocorticoid Receptor Complex | | | | | | | |
|---|---|---|---|---|---|---|---|
| Fraction | ml | mg. protein | dpm* × $10^{-7}$ | specific activity dpm × $10^{-3}$ per mg protein | yield | specific activity | fold pure |
| AFFINITY GEL PROCEDURE | | | | | | | |
| rat liver cytosol | 20 | 550 | 3.64 | 66 | 100% | 1 | 1 |
| affinity gel eluate | 14 | 2.62 | 1.97 | 7,500 | 54% | 113 | 209 |
| TRICOLUMN PROCEDURE | | | | | | | |
| rat liver cytosol | 8.4 | 295 | 2.3 | 78.6 | 100% | 1 | 1 |
| TRICOLUMN | 11 | 0.78 | 1.06 | 13,700 | 46% | 174 | 397 |

*Disintegrations per minute

The receptor complex isolated using the tricolumn has all the characteristics of the unactivated glucocorticoid receptor isolated by other procedures. It activates to the DNA-binding form when sodium molybdate is removed, reacts with a specific monoclonal antibody raised against affinity resin isolated purified receptor, the activated form has associated protein kinase activity which is steroid dependent and binds the ATP analog fluorosulfonylbenzoyl adenosine. The glucocorticoid receptor complex isolated by this process has all the activities and characteristics of the receptor as studied in crude systems and isolated by other methods.

The proteolytic activity of crytosol and tricolumn purified cytosol is determined as described by Ohl et al, *Arch. Biochem. Biophys.*, V 217, 162–173, 1982. Proteolytic activity is reduced by 78% in 90 minutes using the tricolumn process.

TABLE II

Proteolytic Activity of Rat Liver Cytosol Compared to Tricolumn Purified Glucocorticoid Receptor Complex Trichloroacetic Acid Soluble DPM(a)

|  | % Control |
|---|---|
| RAT LIVER CYTOSOL(b) | 100 |
| TRICOLUMN(c) | 22 |

(a) $^{14}$C casein is used as a substrate; cleaved proteolytic products are soluble in 10% TCA.
(b) Cytosol cleaved 45% of total added $^{14}$C casein.
(c) Tricolumn 200 mM potassium phosphate eluate of tricolumn process.

In another experiment, unlabelled receptor is isolated using the tricolumn of this Example and then bound with the covalent affinity ligand [$^3$H]-dexamethasone-21-mesylate (8 Ci/mmol). Fluorescence enhanced radiography is performed and demonstrates that the isolated receptor contains the true steriod binding component of the classical glucocorticoid receptor.

The tricolumn is regenerated by eluting the tightly bound proteins with 2M sodium chloride (approximately 40% of total proteins) then stored in 2M sodium chloride until reequilibrated before reuse as described above.

EXAMPLE 2

Purification of Estrogen Receptor Using the Tricolumn

Ten immature (26 days) female Sprague-Dawley rats are sacrificed by cervical dislocation. The uteri are excised, trimmed, blotted, and weighed at 0° C. The uteri are homogenized in four volumes of Buffer A (w/v; g/ml) by a Virtis homogenizer. The cytosol is then prepared as described for liver in Example 1. The cytosol is labelled two hours with 100 nM [$^3$H]-estradiol (54 Ci/mmol). Thereafter the same process described in Example 1 is followed. The estrogen receptor elutes at the 100 mM potassium phosphate step. Results are summarized in Table III.

TABLE III

|  | ml | mg PROTEIN | Sp. act (dpm/mg) | FOLD PURE Sp. act. | PROTEIN |
|---|---|---|---|---|---|
| UTERINE CYSTOL | 1.8 | 2.7 | 129,947 | 1 | 1 |
| TRICOL. | 2.0 | 0.03 | 23,441,765 | 180 | 90 |

A major 69 kDa band is observed using double stain and SDS-PAGE analysis of the product of the tricolumn process, essentially as described by Puca et al, *J. Steroid Biochem.*, Vol. 12, 105–113, 1980.

while the tricolumn is used here to isolate the unactivated form of the receptor, it can also be used to purify the activated form of the receptor.

The tricolumn is regenerated by eluting the bound proteins with 2 molar sodium chloride (approximately 40% of the total protein) and is stored in 2 molar sodium chloride until used again following equilibration with Buffer A.

EXAMPLE 3

Partial Purification of a Membrane Receptor Using the Tricolumn

Two male Hartley strain guinea pigs (approximately 200 g each) are sacrificed by decapitation. The lungs are quickly removed, weighed and homogenized in 10 volumes (w/v; g/ml) of Buffer B (0.25M sucrose, 50 mM Tris.HCl, 0.5 mM phenylmethyl sulfonylflouride, pH 7.5 at 0° C.), using quick 10 second bursts in a Virtis homogenizer (setting 6). The homogenate is centrifuged at 300 g for 10 minutes and the decanted supernatant is centrifuged at 45,000 g for 20 minutes. The pellet is an enriched membrane fraction.

The enriched membrane fraction is resuspended in one volume of Buffer C [50 mM Tris.HCl (tris(hydroxymethyl)aminomethane hydrochloride), 20 mM $CaCl_2$, pH 7.5 at 0° C.]. Tritiated leukotriene $D_4$ (NEN; 40 Ci/mmol; 5 nM [$^3$H] $LTD_4$) is added to about 4 ml of the enriched membrane friction (2 mg protein/ml) and incubated at 20° C. for 40 minutes. Specific binding is determined by trapping 50 μl of membranes on a GF/A (Whatman) filter and washing twice with about 5 ml of Buffer C, drying the filter and counting in a scintillation counter.

The labelled membranes are centrifuged at 45,000 g for 20 minutes. The pellet is resuspended in detergent [5 mM CHAPS (3-[(3-cholamidopropyl)dimethylammonio]-1-propanesulfonate) in Buffer C] and stirred at 4° C. for 30 minutes. The solubilized suspension is centrifuged at 45,000 g for 20 minutes. The supernatant is placed on a 52 cm × 3.2 cm gel filtration column containing 60 ml A0.5M Biogel resin (Biorad)O. Radioactive fractions are pooled and flowed through a tricolumn as described in Examples 1 and 2. Solubilized membrane receptors elute in the flow-through while other proteins are retained on the column. Results are outlined in TABLE IV.

TABLE IV

Partial Purification of Solubilized $LTD_4$ Receptor from Guinea Pig Lung Membranes

|  | Volume | mg protein | Sp. act (dpm/mg protein) | Fold Pure |
|---|---|---|---|---|
| Membranes | 5 ml | 10.73 | 36,770 | 1 |
| CHAPS Extract | 5 ml | 1.76 | 75,440 | 2 |
| A 0.5 M | 8 ml | .103 | 1,210,000 | 33 |
| Tricolumn | 3 ml | .0034 | 7,554,706 | 205 |

The entire procedure of the foregoing examples which illustrate the invention can be completed in ninety minutes. The process is selective and yields a stable preparation of the receptor.

Any of the components and conditions mentioned as suitable herein can be substituted for its counterpart in the foregoing examples. Although the invention has been described in considerable detail, such detail is for illustration only. Variations can be made by those skilled in the art without departing from the invention except as set forth in the claims.

What is claimed is:

1. A chromatographic column having at least three resin layers between the inlet and the outlet ends of the column, the layer closest the inlet being a strong cationic exchange resin, the middle layer being a backbone containing a triazine dye that will bind proteases and proteins with dinucleotide fold conformations, and the layer closest to the outlet being a weak anionic exchange resin, the ratio of the volumes of the resin layers being 1:2:1.

2. The chromatographic column of claim 1 wherein the resin layer closest to the inlet is a six percent phosphorylated agarose gel crosslinked with epichlorohydrin.

3. The chromatographic column of claim 1 wherein the middle resin layer is a monochlorotriazine dye-containing synthetic matrix.

4. The chromatographic column of claim 3 wherein the matrix is a free radical polymerization product of N-acryloyl-2-amino-2-hydroxymethyl-1,3-propanediol.

5. The chromatographic column of claim 1 wherein the resin layer closest to the outlet is a diethylaminoethyl-containing synthetic matrix.

6. The chromatographic column of claim 4 wherein the matrix is a free radical polymerization product of N-acryloyl-2-amino-2-hydroxymethyl-1,3-propanediol.

7. The chromatographic column of claim 1 wherein the ratio of the volumes of the resin layers is 20:40:20.

8. A construction for rapid one-step isolation and purification of activated and unactivated forms of steroid hormone and cell membrane receptors which comprises a chromatographic column containing a matrix of resin layers between the inlet and the outlet, the resin layer closest to the inlet being a strong cationic exchange resin, the middle layer being a triazine dye containing exchange resin and the layer closest to the outlet being a weak anionic exchange resin, the ratio of the volumes of the resin layers being 1:2:1.

9. The construction of claim 8 wherein the resin layer closest to the inlet is a six percent phosphorylated agarose gel crosslinked with epichlorohydrin.

10. The construction of claim 8 wherein the middle resin layer is a monochlorotriazine dye-containing synthetic matrix.

11. The construction of claim 10 wherein the matrix is a free radical polymerization product of N-acryloyl-2-amino-2-hydroxymethyl-1,3-propanediol.

12. The construction of claim 8 wherein the resin layer closest to the outlet is a diethylaminoethyl-containing synthetic matrix.

13. The construction of claim 12 wherein the matrix is a free radical polymerization product of N-acryloyl-2-amino-2-hydroxymethyl-1,3-propanediol.

* * * * *